(12) United States Patent
Chaumeil

(10) Patent No.: US 12,161,467 B2
(45) Date of Patent: Dec. 10, 2024

(54) SAFETY RELATING TO A MACHINE AND TO A PERSON FITTED WITH A MEDICAL DEVICE

(71) Applicant: Arnaud Chaumeil, Toulouse (FR)

(72) Inventor: Arnaud Chaumeil, Toulouse (FR)

( * ) Notice: Subject to any disclaimer, the term of this patent is extended or adjusted under 35 U.S.C. 154(b) by 869 days.

(21) Appl. No.: 16/479,128

(22) PCT Filed: Dec. 27, 2017

(86) PCT No.: PCT/FR2017/000260
§ 371 (c)(1),
(2) Date: Apr. 28, 2020

(87) PCT Pub. No.: WO2018/122474
PCT Pub. Date: Jul. 5, 2018

(65) Prior Publication Data
US 2020/0245919 A1    Aug. 6, 2020

(30) Foreign Application Priority Data
Dec. 29, 2016   (FR) ...................................... 1670800

(51) Int. Cl.
*A61B 5/00*   (2006.01)
*A61B 5/18*   (2006.01)

(52) U.S. Cl.
CPC .............. *A61B 5/18* (2013.01); *A61B 5/6893* (2013.01); *A61B 5/7405* (2013.01); *A61B 5/742* (2013.01);
(Continued)

(58) Field of Classification Search
CPC . A61B 5/18; A61B 5/746–747; A61B 5/6893; A61B 5/7405; A61B 5/742;
(Continued)

(56) References Cited

U.S. PATENT DOCUMENTS

| 6,480,744 B2 * | 11/2002 | Ferek-Petric ...... A61N 1/37258 340/576 |
| 7,894,476 B2 * | 2/2011 | Doerr ..................... G16H 40/40 370/466 |

(Continued)

FOREIGN PATENT DOCUMENTS

| DE | 10 2014 206960 A1 | 10/2015 |
| EP | 0 560 351 A1 | 3/1993 |

(Continued)

OTHER PUBLICATIONS

International Search Report dated Apr. 6, 2018, issued in PCT Application No. PCT/FR2017/000260, filed Dec. 27, 2017.

*Primary Examiner* — Scott M. Getzow
(74) *Attorney, Agent, or Firm* — Workman Nydegger

(57) ABSTRACT

The safety process covering a vehicle having driving apparatus and a station designed for a person and a person fitted with a medical device, in which: the medical device is designed to work in response to the physiological data of the person with a device and trigger an alarm signal in case of malfunctioning of the medical device per se and alarm signal for any actual or inferred problem regarding the medical condition of the person fitted with a device. A safety module is designed to be associated to the vehicle, to receive data generated by the medical device and generate information matching data received, while the person with a device is associated to the vehicle and the safety module is associated to the vehicle, encrypted communication is established between the medical device and safety module, so that the medical device triggers an alarm signal in case of malfunctioning and/or alarm signal in case of medical problem and so that the safety module generates an alarm notification in line with an alarm signal, one alarm notification at least is thereby transferred to an operator.

22 Claims, 1 Drawing Sheet

(52) U.S. Cl.
CPC ............ *A61B 5/7455* (2013.01); *A61B 5/746* (2013.01); *A61B 2503/22* (2013.01)

(58) Field of Classification Search
CPC ............ A61B 5/7455; A61B 2503/22; B60W 2540/221; B60W 2556/45; B60W 2040/0818; B60W 2540/26; B60W 50/14; B60W 40/08; B60W 2040/0872; B60W 2040/0881; B60W 2300/152; B60K 28/066; B60Y 2200/10; B60Y 2200/221; B60Y 2200/30; B60Y 2200/46; B60Y 2200/51; A61N 1/37; A61N 1/3702; A61N 1/3704; A61N 1/37258
See application file for complete search history.

(56) References Cited

U.S. PATENT DOCUMENTS

| | | | |
|---|---|---|---|
| 8,423,205 | B2 | 4/2013 | Doerr et al. |
| 9,144,389 | B2 | 9/2015 | Srinivasan et al. |
| 9,332,910 | B2 | 5/2016 | Matsunaga et al. |
| 2002/0099424 | A1 | 7/2002 | Ferek-Petric |
| 2005/0148894 | A1 | 7/2005 | Misczynski et al. |
| 2007/0258395 | A1* | 11/2007 | Jollota .................. G16H 20/17 455/67.11 |
| 2009/0171228 | A1* | 7/2009 | Fischell ................. A61B 5/366 600/517 |
| 2009/0171288 | A1 | 7/2009 | Wheeler |
| 2010/0222687 | A1 | 9/2010 | Thijs et al. |
| 2016/0375239 | A1* | 12/2016 | Swerdlow ........... A61N 1/3925 607/5 |
| 2017/0028811 | A1* | 2/2017 | Jayasundera ........ A61B 5/6893 |

FOREIGN PATENT DOCUMENTS

| | | |
|---|---|---|
| GB | 2 534 471 A | 7/2019 |
| WO | 2015/138416 A1 | 9/2015 |
| WO | 2015/160272 A1 | 10/2015 |
| WO | 2016/070981 A1 | 5/2019 |

* cited by examiner

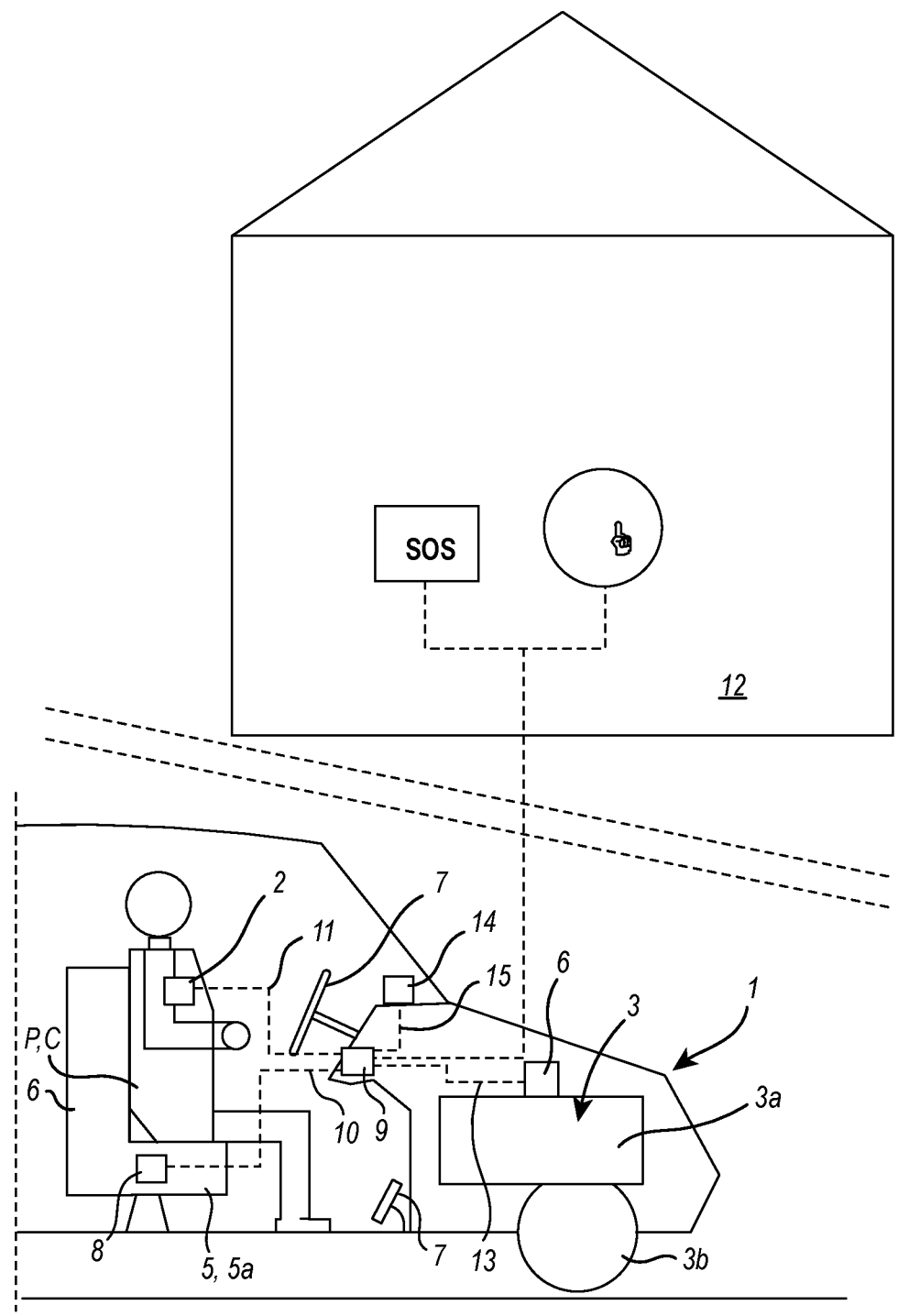

SAFETY RELATING TO A MACHINE AND TO A PERSON FITTED WITH A MEDICAL DEVICE

BACKGROUND OF THE DISCLOSURE

1. The Field of the Disclosure

The invention relates to safety for a vehicle and person fitted with a medical device.

2. The Relevant Technology

The specific purpose of the invention primarily is the safety process designed for a vehicle that comprises driving means and at least one station for one person, including at least one operating station for a person serving the vehicle—in particular the pilot in command—, and at least one person fitted with at least one medical device, considering that the vehicle is designed in such a way that at least one person with a device is associated to the same, at a vehicle station—in particular at the operating station to serve the vehicle. The second purpose of the invention is a safety unit specially designed for the implementation of the process, including a medical device with which a person is fitted and a safety module. The third purpose of the invention is such medical device and such safety module both specially designed for the implementation of the process, as part of the safety unit.

The invention applies to the case of a vehicle such as a land vehicle—such as a motor car, train, tractor, handling vehicle—, sea vehicle—such as a ship—, air vehicle—such as an aircraft—, or spacecraft. The vehicle may also be a crane, for example.

In a manner known per se, such a vehicle comprises driving means such as a motor-driven or propulsion unit to which ordinary means usually associated to the type of vehicle concerned are related, including, without limitation, wheels and transmission means for a land vehicle. It also includes one or more stations for one or more persons, including an operating station (or several operating stations as the case may be) for one person (or more than one person as the case may be) serving the vehicle. A "station" means, for example, a seat and related standard systems. The operating station therefore comprises steering tools such as a remote control, steering wheel, levers, buttons, pedals, etc. "Serving" the vehicle means controlling, steering the vehicle. It is agreed that the person located at the operating station will be referred to as "pilot". The vehicle may also include one or more other stations, other than the operating station, for one or more persons herein usually referred to as "passengers". A person located at a station in the vehicle will be referred to as "associated" to the vehicle.

For example, in the case of a land vehicle such as a motor car, for any driving period, the pilot—in this case the car driver—will sit down on and then remain seated in the driver seat to be able to operate steering units. This also applies to the case of a motor car with some degree of autonomy. Between driving periods, when the car is not driven and not used, the driver will leave the car and be busy with other occupations. From that moment on, he will not be associated to the car, within the meaning given in this case to the word "associated", though he may later be associated to it again. In certain cases, a given driver may use different cars, for periods with brief or long intervals in between, or the driver will have no personal car, as is the case for car rental. What has just been described for a car can be transposed and adjusted to other types of vehicles or crafts.

In the context of the invention, a person who may be or actually is associated to the vehicle (as he is to be found at a station in this vehicle) is fitted with a medical device. It is agreed that such a person will be referred to as a "person with a device".

It can be stated that there are several persons who are or may be associated to the vehicle, and who are fitted with medical devices, as the case may be.

A person who is or may be associated may also be fitted with several medical devices.

In particular, a person with a device is a person who is or may be associated to the operating station to serve the vehicle, i.e., the pilot.

In the context of the invention, such a medical device is designed to work in response to the physiological data of the person with the device and partly or fully remedy any medical problem experienced by the person with a device. Depending on cases, such a medical device will be fitted on the person with a device or placed externally. And this medical device may be used for therapeutic and/or diagnostic purposes. Medical devices falling into the scope of the invention include without limitation: a pacemaker, prosthesis, pump, artificial heart or exoskeleton.

In the context of the invention, "safety" means a situation as objective as possible, relying on medical conditions, resulting in the absence or minimization of hazards or threats.

In the context of the invention, such hazards or threats concern both the person fitted with the medical device, the medical device proper, the vehicle or persons or physical features which may be impacted by the vehicle.

The hazards or threats affecting the person fitted with the medical device are that his medical condition may be more problematic than that expected under predictable circumstances that are under control, when the medical device meets its purpose as expected. Such more problematic condition may indeed be a hazard or threat jeopardizing the very life of the person with a device or a serious or unrecoverable deterioration of his medical condition. In the case where the person with a device is the pilot, hazards or threats are the fact that the pilot is no longer in a position to steer the vehicle properly, with all inherent potential effects this may entail.

Hazards or threats affecting the medical device represent the fact that its performance or—even worse—its operation may be affected, for example due to a structurally or functionally defective part. A typical example is an insufficient charge status for a supply battery, or defective assembly.

Concerning the vehicle, hazards or threats mean those affecting the vehicle, to the extent where its driving means are in operating mode. In fact, if the vehicle is not steered adequately anymore, there is a serious risk of accident and vehicle damage. And in the event of an accident, there is a serious risk that the vehicle might impact persons or physical features on the way of the vehicle.

In the context of the invention, "alarm" means a signal representing a hazard or threat, which can be perceived as such by one—or more—persons and/or one—or more—physical features.

In the context of the invention, it may be considered to use not just one single alarm but multiple alarms corresponding to more or less serious hazards or threats. In such a case, an index of the alarm level will be associated to such an alarm.

Malfunctioning or a problem causing a hazard or threat may be actual. It may only be likely and not be actual yet, in which case it will usually be preceded by warning signs which should also be considered as a cause for alarm.

Though the safety issue is to be considered with the utmost vigilance for the vehicle pilot, it should also be taken into account for the passenger. Indeed, the problematic medical condition of a passenger may, like the pilot's condition, be a hazard or a threat for his very life, in view of any serious or unrecoverable deterioration of his medical condition. In addition, undoubtedly, what affects a passenger may also affect the pilot. So, ultimately, the question of safety is raised for all persons associated to the vehicle.

All the reasons described above lead to the conclusion that safety for a vehicle and a person fitted with a medical device is a crucial problem.

This problem is all the more critical as the number of persons fitted with medical devices will consistently increase. It is also essential to the extent where it would be appropriate to determine adequately bans or restrictions on the use of a vehicle considering that a person who may be associated to such vehicle is fitted with a medical device. Bans or restrictions that are too strict and frequent would be excessive insofar as the occurrence of a hazard or threat would likely be exceptional and as the performance of medical devices is continuously improved and as they are adjusted to each person fitted with a device. Conversely, bans or restrictions on their use which would not be strict enough would be unacceptable considering that preventive safety is considered as an essential and normal necessity.

Document U.S. Pat. No. 8,423,205 describes a safety system comprising an implant, control and vehicle. The vehicle has a control unit which is incorporated into its electronic control system. This control unit is designed to make it possible for a vehicle to operate if a unique identification is received, and to set a vehicle operating mode based on a capability index received, describing the aptitude or a person wearing an implant to use a vehicle. The implant is designed to enter the physiological data of a person wearing an implant. The control device incorporates an initial interface for wireless communications with the implant and a second interface for wireless communications with the control unit of the vehicle. The control apparatus also incorporates a memory for sole identification purposes. In an initial device, the implant is designed to generate a capability index based on physiological data entered and to transfer the capability index to the control apparatus while the initial interface is designed to receive the capability index and the second interface is designed to transfer to the control unit the capability index with the sole identification. In a second device, the implant is designed to transfer physiological data and the control device incorporates a classification unit designed to classify physiological data in one or more capability classes.

The safety system described in Document U.S. Pat. No. 8,423,205 shows many drawbacks and restrictions.

First of all, the sole purpose of this system is to adjust vehicle control to the pilot's condition. Then, this system is first and foremost focused on the vehicle and then on the persons or physical features to be found on the way of the vehicle. However, this system does not directly involve the pilot fitted with the medical device. It does not involve the vehicle passengers either. Finally, it is not focused on medical device malfunctioning proper either.

Then, this system is based on the existence of a single identification which should be registered in the vehicle into which the system is fully incorporated. Then of course, the vehicle is dedicated to one person only, to the extent where it uploaded the system associated to the vehicle with the single identification. This system is therefore not adjusted to cases where the driver has to use different motor cars, for periods with variable intervals, or where the driver has no personal car, as in car rental. In addition, such unique identification can be hacked, which would result in a number of consequences.

Then, though, in an initial built unit of this system, the implant is expected to generate a capability index based on physiological data entered, and transfer such capability index to the control apparatus, in the second built unit, the implant is designed to transfer in a non-encrypted way physiological data whereas the control apparatus has a classification unit intended to classify physiological data in one or more capability classes, which raises serious problems. These physiological data may indeed be hacked and their confidentiality is not guaranteed.

Documents U.S. Pat. Nos. 9,144,389 and 9,332,910 describe safety systems including an implant, control apparatus and a vehicle, where physiological data on the driver are transferred to the vehicle.

Documents EP 0 560 351, WO 2015/160272 describe safety systems based on the detection of the presence or fatigue of the driver.

Document WO 2015/138416 describes a safety system based on a detection system incorporated into the driver's seat. And Documents US 2010/0222687 and US 2005/0148894 rely on detection incorporated into the driver's safety belt.

State of the art technology also includes Documents U.S. Pat. Nos. 7,894,476 and 6,480,744.

None of the systems mentioned above mitigates the drawbacks and restrictions of the safety system described in Document U.S. Pat. No. 8,423,205, quite on the opposite, and none of them meets the expected requirements of effective, modern safety for a vehicle and a person fitted with a medical device.

Document WO2016/070981 describes a system and process used for monitoring the health condition of a person aboard a vehicle. The system includes a control unit comprising: a receiver for the wireless reception of the physiological parameters of at least one unit worn on the body, incorporating one or more sensors to determine one or more physiological parameters of the vehicle occupant and a diagnosis module designed to derive information on the health condition, well-being status or disease incidents, at least partly, though as a requirement, on the basis of physiological parameters received. The control unit is also designed to provide to the vehicle occupant, via at least one on-board output unit, information on the health status, and initiate at least one of the following steps—adjusting vehicle functions to the health condition, or via at least one on-board output unit, offering or undertaking, in an interactive manner, actions to improve such condition. As was mentioned above, this system and process are not focused on the malfunctioning of the control unit proper, which is a medical device. And the aim of this system and process is that the diagnosis module may receive and process the physiological data of the person concerned, which is highly problematic. Not only is the collection of all these data not necessary for safety purposes, but such data may also be hacked and their confidentiality is not guaranteed.

Document GB 2534471 describes a process and includes the stage which implies the provision of a communications protocol for wireless communications between a mobile remote control and control system on a vehicle. Such process does not make it possible to meet the crucial problem of safety involving a vehicle and a person fitted with a medical device on-board. The purpose of this process is to remotely control the vehicle, which is not the purpose of the invention. In addition, this process is not versatile as it is associated to a given vehicle. Possible malfunctioning of the remote control described in the document may only be analyzed because the remote control and vehicle are inseparable.

Document DE102014206960 explains, in relation with a process used to avoid accidents or reduce accident episodes, that the driver's vital signs are determined in a mobile medical apparatus worn by the driver directly or indirectly communicating with a safety system in the vehicle. In the case where vital signs are outside a normal range, an automatic process will be launched in the safety system. As above, this process necessarily transfers and analyses the driver's physiological data, which is highly problematic. And it does not focus on any medical device malfunctioning.

SUMMARY OF THE DISCLOSURE

Then, there is the need, on the one hand, for a safety process involving a vehicle comprising driving means and at least one station for one person, including at least one operating station for a person serving the vehicle—including the pilot-in-command—, and at least one person fitted with at least one medical device, the vehicle being designed so that at least one person with a device, at a station in the vehicle, may be associated with it—in particular at the operating station to serve the vehicle—, and for a safety unit specially designed for the implementation of such process, meeting requirements wanted for effective and modern safety.

These requirements include, without limitation:
Versatility of the application concerning the vehicle which may be a land vehicle—such as a motor car, a train, a tractor, a handling vehicle—, sea vehicle—such as ship—, air vehicle—such as an aircraft—, or spacecraft, or a crane for example.
Versatility of the application concerning the person with a device; this person may be the pilot of the vehicle or a passenger, based on the definitions provided for these two words.
Flexibility concerning the vehicle which will not necessarily be dedicated to the person with a device, who may use different vehicles, at variable intervals, or have no dedicated vehicle.
Versatility of the application to the extent where safety considered may involve one or more persons, and a person may be fitted with one or more medical devices.
Versatility concerning medical devices which may be implanted or located externally, have therapeutic and/or diagnostic purposes.
Versatility concerning hazards or threats with respect both to the person fitted with a medical device, the medical device proper, the vehicle or persons or physical features which may be impacted by the vehicle.
Flexibility to the extent where depending on cases, a sole alarm or multiple alarms corresponding to more or less serious hazards or threats may be considered
Comprehensiveness, to the extent where the problem causing the hazard or threat may either be actual and effective or just be likely and potential
Prevention of hacking of sensitive or physiological data.
Prevention of a massive transfer and storage of data.
Please find below a description of the invention.

First of all, the purpose of the invention is to have a safety process for a vehicle having driving means and at least one station designed for one person, including at least one operating station for one person serving the vehicle—in particular the pilot in command—, and at least one person fitted with at least one medical device, the vehicle being designed so that at least one person with a device may be associated to it, while sitting at a station in the vehicle—in particular the operating station to serve the vehicle—, in which:

There is a medical device designed to work in response to the physiological data of the person fitted with a device and generate, when the occurrence arises, a signal warning of medical device malfunctioning per se and a signal warning of an actual or inferred problem relating to the medical condition of the person fitted with a device, There is a safety module designed to be structurally associated to the vehicle, to receive data generated by the medical device while the person fitted with a device is associated to the vehicle, and generate information matching data received, the medical device and safety module are such that the safety module works without receiving or storing the physiological data of the person fitted with a medical device, making this non-compulsory, while the person with a device is associated to the vehicle and the safety module is associated to the vehicle, encrypted communication is established between the medical device and safety module, so that the medical device triggers—when this is justified—a signal warning of malfunctioning and/or signal warning of an actual or inferred medical problem and so that the safety module generates at least one alarm notification corresponding to an alarm signal, one alarm notification at least is thereby transferred to an operator.

According to one built system, we have a medical device designed to generate, based on the occurrence, one among several signals warning of medical device malfunctioning and/or one among several signals warning of an actual or inferred problem concerning the medical condition of the person fitted with a device, in which an index of the alarm level is associated to one alarm signal among several ones.

Based on one built system, we have a medical device which is either implanted in or is external to the person fitted with a device, for therapeutic and/or diagnostic purposes.

Based on one built system, either the person with a device occupies an operating station in the vehicle or we have a vehicle that comprises at least one station other than the operating station, in which the person with a device occupies a station other than the operating station.

Based on one built system, we have a medical device and a safety module such that the safety module does not receive or store the physiological data of the person fitted with a device.

Based on one built unit, we have a medical device and a safety module such that the transfer between the medical device and safety module is automatically established merely as a result of the presence of the person with a device at a station in the vehicle and, as the case may be, of the activation of the safety module.

Based on one built system, we have a medical device and a safety module such that the transfer between the medical device and safety module is automatically established, as the case may be, without the required and systematic necessity of a matching operation or transfer of a single identifier, as the case may be, in return for a consistency check (with the possibility of using, as the case may be, an artificial intelligence process) between the medical device of the person fitted with a device and the medical device as perceived by the safety module.

Based on one built system, we have a safety module designed with no memory or with no long-term memory for the physiological data of the person fitted with a device, or for a single identifier designed for a matching operation on the one hand, and any signal warning of medical device malfunctioning per se or a signal warning of an actual or inferred problem concerning the medical status of the person with a device on the other hand.

Based on one built system, we have either a portable safety module, structurally associated to the vehicle in a removable fashion; we structurally dissociate the safety module from the vehicle when the person with a device is not at a station in the vehicle and we structurally associate the safety module to the vehicle on a temporary basis when the person with a device is at a station in the vehicle or we have a safety module structurally associated to the vehicle fixed in place, on a permanent basis.

Based on one built system, we thereby transfer at least one alarm notification to an operator selected as a control unit for the operation of the driving means of the vehicle, and/or a person at a station in the vehicle, and/or remote alarm system of the vehicle.

Based on one built system, we have a vehicle incorporating a control unit for the operation of its driving means functionally associated to the safety module, were thereby transfer at least one alarm notification to the control unit and we program the control unit so that it controls the driving means based on the occurrence of a signal warning of medical device malfunctioning and/or signal warning of an actual or inferred medical problem and alarm level index in the case of one alarm signal among several ones.

Based on one built system, we have a control unit which is either programmable—we previously program the control unit based on a scenario or scenarios according to the alarm signal—or which is pre-programmed based on one or more scenarios according to the alarm signal.

Based on one built system, we have a sensory signal functionally associated to the safety module designed to generate an alarm signal which can be perceived by a person at a station in the vehicle, such as a visual, sound, vibration or comparable device.

Based on one built system, we have a remote alarm system for the vehicle—we remotely transfer to the alarm system at least one alarm notification, we generate vehicle geo-location data and we remotely transfer to the alarm system the geo-location data.

Based on one built system, we detect the presence of one person at a station in the vehicle.

Based on a second aspect, the invention relies upon a safety unit relating to a vehicle incorporating driving means and at least one station for one person, including at least one operating station for a person serving the vehicle—in particular the pilot in command—, and at least one person fitted with at least one medical device, the vehicle being designed so that at least one person with a device may be associated to the same, while being at a station in the vehicle—in particular at the operating station to serve the vehicle—, for the implementation of the process which has just been described, such as:

the medical device is designed to operate in response to the physiological data of the person with a device and to generate, when the occurrence happens, a signal warning of malfunctioning affecting the medical device per se and a signal warning of an actual or inferred problem concerning the medical status of the person with a device, it includes a safety module designed to be structurally associated to the vehicle, to receive data generated by the medical device while the person with a device is associated to the vehicle, and to generate information in line with the data which it receives so that the medical device may generate—when this is justified—a signal warning of any malfunctioning and/or signal warning of an actual or inferred medical problem and so that the safety module may generate at least one alarm notification in line with an alarm signal, it includes means to encrypt communications between the medical device and safety module, it includes ways to transfer from there at least one alarm notification to an operator, the medical device and the safety module are such that the safety module is operated without receiving or storing the physiological data of the driver fitted with the medical device making this non-compulsory Based on a built system, the medical device is designed to generate, based on the occurrence, the signal—among others—warning of medical device malfunctioning and/or the signal—among several ones—warning of an actual or inferred problem concerning the medical condition of the person with a device, and in which an alarm level index is associated to an alarm signal, among others.

Based on a built system, the safety module is designed with no memory or with no long-term memory for the physiological data of the person with a device, signal warning of any malfunctioning of the medical device per se on the one hand, or signal warning of an actual or inferred problem concerning the medical condition of the person with a device on the other hand.

Based on a built unit, the safety module is designed with no memory or with no long-term memory for a single identifier and/or designed with a device to ensure that the medical device of the person with a device is consistent with the medical device as perceived by the safety module.

Based on built units, the safety module is either portable, structurally associated to the vehicle in a removable fashion, or structurally associated to the vehicle in a fixed, permanent way.

Based on a built unit, the unit includes an operator selected as one or more of the following: a control unit for the operation of the driving means of the vehicle, a person at a station in the vehicle, remote alarm system of the vehicle.

Based on a built unit, the vehicle incorporates a control unit for the operation of its driving means functionally combined with the safety module, and said control unit is either programmable or pre-programmed.

Based on a built unit, the safety unit incorporates a sensory alarm functionally combined with the safety module designed to generate an alarm signal which may be perceived by a person at a station in the vehicle, such as a visual, sound, vibration or comparable means.

Based on a built unit, the safety unit includes a remote alarm system for the vehicle and vehicle geo-location system.

Based on a built unit, transfer means between the medical device, safety module, means of transfer to an operator are of the wireless or wired type.

Based on a built unit, the safety unit further includes means used to detect the presence of a person at a station in the vehicle, functionally combined to the safety module.

Based on built units, the vehicle is a land vehicle—such as a motor car, train, tractor, handling vehicle—, sea vehicle—such as a ship—, air vehicle—such as an aircraft—, or spacecraft.

Based on a third aspect, the invention relies on a medical device specially designed for the implementation of the previously described process, designed to operate in response to the physiological data of the person with a device and generate, when the occurrence arises, a signal warning of medical device malfunctioning per se and a signal warning of an actual or inferred problem relating to the medical status of the person with a device, as the case may be, among several alarm signals and the medical device is designed to be implanted either externally, for a therapeutic and/or diagnostic purpose.

Based on a fourth aspect, the invention relies on a safety module specially designed for the implementation of the safety process which has just been described, designed to receive data generated by a medical device and to generate information in line with the data received.

The invention enables a machine-to-machine dialogue without requiring any human action in its normal and usual operating mode. If the invention involves a medical device and a vehicle, each one of them will primarily fulfil its own role, irrespective of the other, and the safety module will be used as an intermediary between them for safety purposes, without exercising any specific medical diagnosis function and without exercising any function of control of the vehicle proper.

BRIEF DESCRIPTION OF THE DRAWINGS

FIG. 1, which is unique, is a strictly diagrammatical view illustrating the invention.

DETAILED DESCRIPTION ON THE PREFERRED EMBODIMENTS

We are now describing a possible particular version of the invention as an example.

This built unit does not exclude others, as the man in the trade can transpose and adapt conclusions drawn from the description of the particular built unit described to other built units.

The invention relies upon a safety process, a safety unit specially designed for the implementation of the process, a medical device and a safety module both specially designed for the implementation of the process and, thereby for being part of the safety unit. Later, the description, to the extent where it relates to the safety process, is valid for the safety unit as well as the medical device and safety module, and conversely, the description, to the extent where it relates to the safety unit, medical device and safety module, is valid for the safety process.

As stated, "safety" means a situation as objective as possible, relying on medical conditions, resulting in the absence or minimization of hazards or threats with respect both to the person fitted with a medical device, the medical device proper, the vehicle or persons or physical features which can be impacted by the vehicle.

It is agreed that the invention relies on any means mentioned as operating stage or physical feature as well as any functionally equivalent means.

It is agreed that it is not required to describe in detail such or such means mentioned, to the extent where the indication of its relevance or role or of the effect generated or implementation is enough for the man in the trade to be able to achieve it.

In general, the purpose of the invention is to ensure the safety of a vehicle incorporating driving means and at least one station for a person, including at least one operating station for a person serving the vehicle—including the pilot in command—, and at least one person fitted with at least one medical device, the vehicle being designed so that at least one person with a device may be associated to the same while being at a station in the vehicle—in particular at the operating station to serve the vehicle.

Such a vehicle may be a land vehicle—such as a motor car, train, tractor, handling vehicle—, sea vehicle—such as a ship—, air vehicle—such as an aircraft—, or spacecraft, or a crane for example.

The person fitted with a device may equally be the pilot of the vehicle or a passenger, based on the definitions given to these two words.

The vehicle will not necessarily be dedicated to the person fitted with a device, and such person may use different vehicles, at varying intervals, or have no dedicated vehicle.

The safety considered may be related to one or more persons—a person may be fitted with one or more medical devices.

Medical devices may be implanted or located externally, have therapeutic and/or diagnostic purposes.

The hazards or threats targeted by the safety on which the invention is focused relate both to the person fitted with a medical device, the medical device proper, the vehicle or persons or physical features which may be impacted by the vehicle.

The problem causing any hazard or threat may be actual and undeniable or just be likely and potential.

The particular built unit described refers to the specific case of a land vehicle such as a motor car (1), the driver (C) fitted with a medical device (2).

The motor car (1) has driving means (3) such as an engine (3a) to which ordinary means such as wheels (3b) and transmission are associated. The motor car (1) also includes a control unit (4) to operate its driving means (3).

The motor car (1) has at least one station (5) for one person (P), including at least one operating station (5a), i.e., in this case, a driver station (5a), for the person serving the motor car, namely the driver (C).

A station (5) typically includes a seat (6) and related ordinary means. So, the driving station (5a) incorporates such a seat (6) and steering means (7) such as a remote control, steering wheel, levers, buttons, pedals, etc.

For any period of driving of the motor car (1), the driver (C) will be associated to the motor car to the extent where he will sit down and remain seated on the seat (6) of the driver station (5a), to be able to manoeuvre steering units (7). Between driving periods, when the motor car (1) is stationary and is not used, the driver (C) will leave the motor car (1) to be involved in other activities. He will then no longer be associated to the motor car (1), in line with the meaning given in this case to the word "associated". The driver (C) may still be associated to the motor car (1) later.

The medical device (2) has been designed to operate in response to the physiological data of the driver (C) and generate, when the occurrence arises, a signal warning of malfunctioning affecting the medical device (2) per se and a signal warning of an actual or inferred problem concerning the medical condition of the driver (C).

Such a medical device (2) is either implanted or is external to the driver (C). It is for therapeutic and/or diagnostic purposes. Such medical devices (2) include, without limitation: a pacemaker, prosthesis, pump, artificial heart, exoskeleton.

Based on a built unit, the medical device (2) is designed to generate a single signal warning of any malfunctioning affecting the medical device and/or single signal warning of a problem relating to the medical condition of the driver (C).

Based on another built unit, the medical device (2) is designed to generate, depending on the occurrence, one signal—among several ones—warning of malfunctioning affecting the medical device and/or one signal—among several ones—warning of a problem relating to the medical condition of the driver (C). In such a built unit, an alarm level index will be associated to an alarm signal among several ones.

Based on a built unit, the signal warning of a problem affecting the medical status of the driver (C) is an actual, undeniable problem. Based on another built unit, there is a possibility that it is only likely and potential—then it is usually preceded by warning signs.

In a built unit, there are means (8) to detect the presence of the driver (C) at the driver station (4a). For example, such presence detection means (8) are associated to the driver's seat (C).

In that way, the safety process has a system for detecting the presence of the driver (C) at the driver station (5a).

The process implements and the safety system also includes a safety module (9).

The safety module (9) has been designed to be structurally associated to the motor car (1).

In the case where there are means (8) used to detect the presence of the driver (C) at the driver station (5a), there is a transfer (10) between detection means (8) and the safety module (9). It is thereby possible to automatically activate the safety module (9) in another way than by activating the medical device (2).

Based on a built unit, the safety module (9) is portable and structurally associated to the motor car (1) in a removable fashion. The safety module (9) will then be structurally dissociated from the motor car (1) when the driver (C) is not at the driver station (5a). Conversely, the safety module (9) is structurally associated to the motor car (1) on a temporary basis when the driver (C) is at the driver station (5a).

Based on another built unit, the safety module (9) is structurally associated to the motor car (1) in a fixed and permanent way.

The safety module (9) has been designed to receive data generated by the medical device (2), when the driver (C) is at the driver station (5a).

The safety module (9) has also been designed to generate information matching the data received from the medical device (2).

There are also transfer means (11) between the medical device (2) and safety module (9), so the safety process incorporates a transfer between the medical device (2) and the safety module (9).

The safety unit too has means for encrypting communications between the medical device (2) and safety module (9). This building arrangement makes it possible to avoid the hacking of data transferred and guarantees data confidentiality.

With means previously described, the medical device (2) generates—when this is justified—a signal warning of any malfunctioning and/or signal warning of a problem. And the safety module (9) functionally associated to the medical device (2), as stated, will in its turn generate at least one alarm notification in line with an alarm signal.

The safety process is such that at least one alarm notification is thereby transferred to an operator, as the safety unit has means for transferring said alarm notification to the operator.

The relevant operator will be selected as one or more from the list below: the control unit (4) for the operation of the driving means (3) of the motor car (1), the driver (C) is at the driver station (5a) or a passenger in the motor car (1), or remote alarm system (12) for the motor car (1). And the safety unit incorporates one or more operators (4, C & 12).

In the case where the operator is the control unit (4), the control unit (4) will be functionally associated to the safety module (9) by transfer means (13). The alarm notification will later be transferred to the control unit (4).

In a built system, such control unit (4) is programmable and we program it before based on one or more scenario(s) depending on the triggering of a signal warning of malfunctioning affecting the medical device (2) and/or a signal warning of a medical problem suffered by the driver (C), as the case may be, taking into account the alarm level index in the event of an alarm signal among several alarm signals.

In another built system, this control unit (4) is pre-programmed according to such scenario(s).

In the case where the operator is the driver (C) sitting at the driver station (5a) or a passenger in the motor car (1), the unit incorporates a sensory alarm system (14), functionally associated to the safety module (9) by transmission means 15. Such a sensory alarm system (14) is designed to generate an alarm signal which may be perceived by a person at a station (4) in the motor car (1), including the driver (C). This may be, for example, a visual, sound, vibration means or generally any other comparable means. Then the safety process is such that via the sensory alarm system (14), an alarm signal perceptible by the relevant person is triggered.

In the case where the operator is the driver, there is a distant alarm system (12) separate from the motor car, the safety unit incorporates such an alarm system (12).

Such an alarm system (12) is functionally associated to the safety module (9) via transfer systems (16). Such alarm system (12) is designed in such a way that the alarm notification is remotely transferred to the same. In addition, the safety module is arranged in such a way as to be able to directly generate geo-location data for the motor car (1) and remotely transfer them to the alarm system (12).

Such an alarm system (12) may be more or less distant from the motor car (1), e.g., several kilometres or dozens of kilometres away.

Such an alarm system (12) may, for example, be an emergency centre with maps, diagnosis tools and, as the case may be, emergency staff. So, in case of any hazard or threat corresponding to an alarm signal, such an emergency centre may act and find the motor and rescue the driver (C).

In a built system, the medical device (2) and safety module (9) are such that the transfer between the medical device (2) and safety module (9) is automatically established due to the mere presence of the driver on the driver station seat (6), thanks to detection means (8).

The safety module (9) may also be activated following the receipt of a signal from the medical device (2).

So, with the standard system, the process and system are such that it is not necessary to plan a matching operation or the transfer of a sole identifier.

However, as the case may be, we will check the consistency between the medical device (2) of the driver (C) and the medical device as perceived by the safety module (9), as the safety module (9) is designed with a device to check on such consistency.

The medical device (2) and safety module (9) are such that the safety module (9) works without receiving or storing the physiological data of the driver (C) fitted with the medical device (2), which guarantees the confidentiality of such data. Similarly, the process used for the operation does not require in any way the compulsory dispatch of physiological data to the safety module.

So, the safety module (9) is designed with no memory or no long-term memory for the physiological data of the driver (C), or for a sole identifier intended for a matching operation, any alarm signal warning of any malfunctioning of the medical device per se on the one hand or an alarm signal for a problem relating to the medical status of the driver (C) on the other hand.

Based on built systems, transfer systems (10, 11, 13 & 15) are wireless or wired.

These transfer means are compatible with a protocol or standard concerning transfers in the medical area as the case may be.

The invention claimed is:

1. A safety process relating to a vehicle incorporating driving means, a control unit to operate the driving means, and at least one station designed for one person, and at least one person being fitted with at least one medical device associated to the vehicle, in which:
    the medical device is designed to work in response to physiological data of the person fitted with a medical device,
    a safety module designed to be structurally associated to the vehicle, which may be activated and generates at least one alarm notification,
    transmission is established between the medical device and the safety module, wherein:
    the medical device is either implanted or external to the person fitted with the medical device,
    the medical device triggers, when the occurrence arises, alarm signal warnings of malfunctioning affecting the medical device and alarm signal warnings of an actual or inferred problem relating to the medical status of the person fitted with the medical device,
    the transfer between the medical device and safety module is automatically established due to the mere presence of the person fitted with the medical device by a detector mounted to the vehicle, the detector being external to the medical device and coupled to the safety module, or the safety module is activated following the receipt of a signal from the medical device, and when activated, the safety module receives data generated by the medical device, and generates information matching the data received,
    an alarm level index is associated to the alarm signal warnings,
    the safety module is used for safety purposes relying on medical conditions, resulting in the absence or minimization of hazards or threats with respect both to the person fitted with the medical device, the medical device itself, the vehicle or persons or physical features which can be impacted by the vehicle,
    the safety module is used for safety purposes, without exercising any specific medical diagnosis function and without exercising any function of control of the vehicle proper,
    the safety module is such that the safety module operates without receiving or storing the physiological data of the person fitted with a medical device,
    encrypted communication is established between the medical device and the safety module, so that the medical device passes an alarm signal to the safety module when the medical device detects malfunctioning of the medical device and/or actual or inferred medical problem to the person,
    the safety module generates at least one alarm notification in line with an alarm signal so that at least one alarm notification is thereby transferred to an operator being the control unit for the operation of the driving means, functionally associated to the safety module, such control unit being programmed based on one or more scenario(s) depending on the triggering of a signal warning of malfunctioning taking into account the alarm level index,
    the safety process relating to a vehicle being automatic without requiring any human action.

2. The safety process based on claim 1, in which the medical device is for therapeutic and/or diagnostic purposes.

3. The safety process based on claim 1, where the person fitted with the medical device occupies the operating station in the vehicle.

4. The safety process based on claim 1, wherein the medical device and the safety module are configured such that the communication between the medical device and the safety module is automatically established without the compulsory and systematic necessity of a matching operation or transfer of a sole identifier, consistency being is checked, using an artificial intelligence process, between the medical device of the person fitted with the medical device and the medical device as perceived by the safety module.

5. The safety process based on claim 1, in which the safety module is designed with no long-term memory for physiological data of the person with the medical device or for a sole identifier intended for a matching operation.

6. The safety process based on claim 1, further comprising safety module being structurally associated to the vehicle in a removable fashion, so that the safety module can be structurally dislocated from the vehicle when the person fitted with the medical device is not at a station in the vehicle.

7. The safety process based on claim 1, wherein the operator comprises a person in a station of the vehicle and/or, remote alarm system for the vehicle.

8. The safety process based on claim 1, in which a sensory alarm system, functionally associated to the safety module, is designed to generate an alarm signal which can be perceived by a person at a station in the vehicle, including at least one of a visual, sound, or vibration.

9. The safety process based on claim 1, further comprising a remote alarm system in the vehicle; the alarm notification being remotely transferred to the alarm system, geo-location data being generated for the vehicle and the geo-location data are remotely transferred to the alarm system.

10. A safety unit relating to a vehicle incorporating driving means, a control unit to operate the driving means, and at least one station designed for one person, and at least one person being fitted with at least one medical device associated to the vehicle, in which:
    the medical device is designed to work in response to physiological data of the person fitted with a medical device,
    a safety module designed to be structurally associated to the vehicle, which may be activated and generates at least one alarm notification,
    transmission is established between the medical device and the safety module, wherein:
    the medical device is either implanted or external to a person who is fitted with, the medical device triggers, when the occurrence arises, alarm signal warnings of malfunctioning affecting the medical device and alarm signal warnings of an actual or inferred problem relating to the medical status of the person fitted with the medical device, the transfer between the medical device and safety module is automatically established due to the mere presence of the person fitted with the medical device thanks to a detector mounted to the vehicle, the detector being external to the medical device and coupled to the safety module, or the safety module is activated following the receipt of a signal from the medical device, and when activated, the safety module receives data generated by the medical device, and generates information matching the data received, an alarm level index is associated to an alarm signal, the safety module is used for safety purposes relying on medical conditions, resulting in the absence or minimization of hazards or threats with respect both to the person fitted with the medical device, the medical device itself, the vehicle or persons or physical features which can be impacted by the vehicle, the safety module is used for safety purposes, without exercising any specific medical diagnosis function and without exercising any function of control of the vehicle proper, the safety module is such that the safety module operates without receiving or storing the physiological data of the person fitted with a medical device, encrypted communication is established between the medical device and the safety module, so that the medical device passes an alarm signal to the safety module when the medical device detects malfunctioning of the medical device and/or actual or inferred medical problem to the person, and the safety module generates at least one alarm notification in line with an alarm signal so that at least one alarm notification is thereby transferred to an operator being the control unit for the operation of the driving means, functionally associated to the safety module, such control unit being programmed based on one or more scenario(s) depending on the triggering of a signal warning of malfunctioning taking into account the alarm level index, the safety process relating to a vehicle being automatic without requiring any human action.

11. The safety unit based on claim 10, in which the safety module is designed with no long-term memory for the physiological data of the person fitted with a medical device or any alarm signal in case of malfunctioning of the medical device or an alarm signal for any actual or inferred problem regarding the medical condition of the person with the medical device.

12. The safety unit based on claim 10, in which the safety module is designed with no long-term memory for a single identifier and/or designed with a system to ensure that the medical device of the person fitted with the medical device is consistent with the medical device as sensed by the safety module.

13. The safety unit based on claim 10, in which the safety module is either portable, structurally associated to the vehicle in a removable fashion, or structurally associated to the vehicle in a fixed permanent way.

14. The safety unit based on claim 10, comprising a sensory alarm system, functionally associated to the safety module, designed to generate an alarm signal perceptible by the person at a station in the vehicle, including at least one of a visual, sound, or vibration.

15. The safety unit based on claim 10, comprising a remote alarm system for the vehicle and a vehicle geo-location system.

16. The safety unit based on claim 10, in which communication means between the medical device, safety module, and a transfer means to an operator are wireless systems.

17. The safety unit based on claim 10, further including means for detecting the presence of a person at a station in the vehicle, functionally associated to the safety module.

18. The safety unit based on claim 10, in which the vehicle is a land vehicle, a sea vehicle, air vehicle, or space craft.

19. A medical device for the implementation of the safety process according to claim 1, either implanted or external to a person who is fitted with, be used for therapeutic and/or diagnostic purposes, designed to work in response to the physiological data of the person fitted with a medical device and trigger, when the occurrence arises, alarm signal warnings of malfunctioning affecting the medical device and alarm signal warnings of an actual or inferred problem related to the medical status of the person with a medical device.

20. A safety module for the implementation of the safety process based on claim 1, designed to receive data generated by a medical device and to generate information with the data received to generate an alarm signal.

21. A safety process relating to a vehicle incorporating driving means and at least two stations designed for receiving a person fitted with a medical device, the at least two stations comprising an operating station for receiving the person when the person will be operating the vehicle and a passenger station for receiving the person when the person will not be operating the vehicle, in which:

the medical device is designed to work in response to physiological data of the person fitted with the medical device and trigger, when the occurrence arises, an alarm signal warning of malfunctioning affecting the medical device and an alarm signal warning of an actual or inferred problem relating to the medical status of the person fitted with the medical device, a safety module is structurally associated to the vehicle, to receive data generated by the medical device as the person fitted with the medical device is associated to the vehicle, the safety module is automatically activated when the person fitted with the medical device is detected by a detector mounted to the vehicle, the detector being external to the medical device and coupled to the safety module, the safety module is such that the safety module operates without receiving or storing the physiological data of the person fitted with a medical device, wherein, as the person fitted with the medical device is received within the operating station or the passenger station:

the safety module is automatically activated based on the detection of the person by the detector;

the safety module is associated with the medical device;

the safety module determines whether the person is received in the operating station or the passenger station;

encrypted communication is established between the medical device and the safety module, so that the medical device passes an alarm signal to the safety module when the medical device detects malfunctioning of the medical device and/or an actual or inferred medical problem of the person; and the safety module generates at least one alarm notification in line with an alarm signal so that at least one alarm notification is thereby transferred to an operator.

22. The safety process based on claim 21, wherein the at least one alarm notification generated by the safety module is dependent on whether the person is detected as being received in the operating station or the passenger station.

* * * * *